(12) United States Patent
Shevchenko et al.

(10) Patent No.: US 8,133,356 B2
(45) Date of Patent: Mar. 13, 2012

(54) METHOD OF MONITORING MICROBIOLOGICAL DEPOSITS

(75) Inventors: Sergey M. Shevchenko, Aurora, IL (US); Michael J Murcia, DeKalb, IL (US); Patrick J. Macuch, Naperville, IL (US)

(73) Assignee: Nalco Company, Naperville, IL (US)

( * ) Notice: Subject to any disclaimer, the term of this patent is extended or adjusted under 35 U.S.C. 154(b) by 891 days.

(21) Appl. No.: 12/142,369

(22) Filed: Jun. 19, 2008

(65) Prior Publication Data

US 2009/0314445 A1 Dec. 24, 2009

(51) Int. Cl.
*D21H 23/78* (2006.01)
*D21H 23/08* (2006.01)
*D21H 21/36* (2006.01)

(52) U.S. Cl. .......... 162/198; 162/161; 73/61.62; 435/40

(58) Field of Classification Search ................... 162/198, 162/199, 263, 272, 274, 4, 5, 161, 164.3; 73/61.45, 61.49, 61.61, 61.62, 61.75, 61.79, 73/64.53; 435/34, 39, 40
See application file for complete search history.

(56) References Cited

U.S. PATENT DOCUMENTS

| | | | | |
|---|---|---|---|---|
| 5,135,852 | A * | 8/1992 | Ebersole et al. | ................ 435/39 |
| 5,201,215 | A | 4/1993 | Granstaff | |
| 6,053,032 | A | 4/2000 | Kraus | |
| 7,842,165 | B2 | 11/2010 | Shevchenko | |
| 2006/0281191 | A1 * | 12/2006 | Duggirala et al. | ............ 436/178 |
| 2009/0056897 | A1 * | 3/2009 | Shevchenko et al. | ......... 162/198 |
| 2011/0073263 | A1 | 3/2011 | Shevchenko | |

FOREIGN PATENT DOCUMENTS

| | | |
|---|---|---|
| EP | 1076238 | 2/2001 |
| WO | 03016556 | 2/2003 |
| WO | 2006135612 | 12/2006 |
| WO | 2009032561 | 3/2009 |

OTHER PUBLICATIONS

International Search Report for PCT/US2009/047730.

* cited by examiner

*Primary Examiner* — Eric Hug

(74) *Attorney, Agent, or Firm* — Joshua D. Bishop; Michael B. Martin

(57) ABSTRACT

A method for monitoring one or more deposits including microbiological deposits on a surface immersed in an aqueous medium of a process is disclosed. The method comprises: (a) providing a QCM that is in contact with an aqueous medium, wherein said QCM has a top side surface contacting the aqueous medium, and a second, bottom side surface isolated from the aqueous medium; (b) providing a composition that is selective for one or more deposit types, including microbiological deposits without the use of an antigen or an antibody; (c) applying said composition to the top side of said QCM surface; (d) measuring the rate of deposition of said deposits from the aqueous medium onto the top side of said QCM surface; and (e) optionally taking corrective action to change one or more process parameters, or chemistry applied to the process, or a combination thereof, to achieve a desired result in regards to microbiological deposition.

21 Claims, No Drawings

METHOD OF MONITORING MICROBIOLOGICAL DEPOSITS

FIELD OF THE INVENTION

The invention pertains to a method for monitoring one or more deposits including microbiological deposits, specifically but not exclusively targeting pulp and paper applications.

BACKGROUND OF THE INVENTION

The deposition of microbiological materials in an aqueous stream is often problematic to the proper function of a process that contains the aqueous stream. Various techniques have been deployed for measuring organic and inorganic deposition in papermaking processes, but these techniques often lack the selectivity necessary to differentiate a biological deposit from a general organic/inorganic deposit such as pitch or stickies. As a result of this lack of sensitivity, current protocols do not have the sensitivity to capture the deposition environment of dynamic processes such as papermaking processes. Therefore, an improved method of monitoring deposits is needed in the art of process stream deposition control.

SUMMARY OF THE INVENTION

The present invention provides for a method for monitoring one or more deposits including microbiological deposits on a surface immersed in an aqueous medium comprising: (a) providing a QCM that is in contact with an aqueous medium, wherein said QCM has a top side surface contacting the aqueous medium, and a second, bottom side surface isolated from the aqueous medium; (b) providing a composition that is selective for one or more deposit types, including microbiological deposits without the use of an antigen or an antibody, (c) applying said composition to the top side of said QCM surface; (d) measuring the rate of deposition of said deposits from the aqueous medium onto the top side of said QCM surface; and (e) optionally taking corrective action to change one or more process parameters, or chemistry applied to the process, or a combination thereof, to achieve a desired result in regards to microbiological deposition.

DETAILED DESCRIPTION OF THE INVENTION

Definitions

"Papermaking process" means a method of making any kind of paper products (e.g. paper, tissue, board, etc.) from pulp comprising forming an aqueous cellulosic papermaking furnish, draining the furnish to form a sheet and drying the sheet. The steps of forming the papermaking furnish, draining and drying may be carried out in any conventional manner generally known to those skilled in the art. The papermaking process may also include a pulping stage and/or a bleaching stage. The papermaking furnish may include recycled pulp.

"QCM" means quartz crystal microbalance. A quartz crystal microbalance is analytical tool. As an example, a discussion of a quartz crystal microbalance is found in the text of U.S. Pat. No. 5,201,215, which is herein incorporated by reference. In general, a quartz crystal microbalance has a crystal that resonates at a frequency which is reduced by depositing mass. The reduction in frequency is converted to a measurement that characterizes the deposition, e.g. the amount of the deposition.

Preferred Embodiments

As stated above, the present invention provides for a method for monitoring one or more deposits including microbiological deposits on a surface immersed in an aqueous medium of a process.

The methodology of the present invention may be applied to various types of processes.

In one embodiment, the process is a papermaking process.

In another embodiment, the aqueous medium of a process contains pulp slurry and/or waters from any stage of a papermaking process.

The methodology of the present invention requires providing a composition that is selective for one or more types of deposits, including microbiological deposits without the use of an antigen or an antibody; and applying said composition to the top side of said QCM surface.

The application of the composition to the QCM can be carried out by various mechanisms that would be appreciated by one of ordinary skill in the art. For example, the composition, e.g. a polymer-based composition, may be applied to the QCM surface by a spin coating technique or by an apparatus that facilitates the application of the composition to the QCM surface. It can be also applied by a simplified method such as dropping a composition solution from a height, which provides for a relatively even distribution of the solution over the crystal surface.

The composition applied to the surface of the QCM contains one or more types of compositions. For example, nutrients, biocides and various types of polymers are applied to the top side of the QCM surface.

In one embodiment, the composition contains one or more nutrients and/or biocides.

In another embodiment, the composition contains nutrients that are selected from the group consisting of: biosynthesis metabolites; carbohydrates; polysaccharides; amines; organic acids; alcohols; inorganic nitrogen, sulfur, potassium, sodium, calcium, magnesium, phosphorous, iron, copper, and/or manganese compounds; and a combination thereof.

In another embodiment, the composition contains one or more elements for promoting and/or suppressing microbiological growth of one or more microorganisms that deposit from the aqueous medium onto or grow on the top side of the QCM surface.

In another embodiment, the composition applied to the QCM surface contains at least one of the following compositions: halogen based biocides; hypochlorites; hypobromites; chloroamines; bromoamines; chlorosulfamates; bromosulfmates; aldehydes; parabens; acid-anionic compounds; diamines; metals; quaternary ammonium compounds; chlorohexadine; dyes; alcohols; phenols; cresols; organic acids; and esters.

In another embodiment, the composition applied to the QCM surface contains one or more components that suppress the growth rate of one or more bacteria, and wherein said components are selected from at least one of following chemistries: biocides, surfactants, polymers, organic acids, and a combination thereof.

In another embodiment, the composition applied to the surface of the QCM promotes the growth of one or more microorganisms, and wherein the composition is selected from the group consisting of: iron salts for filamentous bacteria; lactic acid and/or sulfate for sulfate reducing bacteria; and starch and cellulose for species common to paper machine fouling. One of ordinary skill in the art will be knowledgeable of species common to paper machine fouling.

In a further embodiment, the microorganisms are myxobacteria.

In a further embodiment, the filamentous bacteria is selected from the group consisting of: *Sphaerotillus; Crenothrix; Leptothrix; Gallionella*; Herpetosiphon; and Haliscomenobacter.

In another embodiment, the composition comprises one or more coating polymers.

In another embodiment, the coating polymers are cured epoxy resins containing one or more epoxy resins and one or more curing agents. Curing can be achieved by keeping the coated surface under ambient conditions for a certain time or accelerated photochemically or thermally.

In another embodiment, the epoxy resins are derived from epichlorohydrin and bisphenol A; and resins containing aromatic, aliphatic, cycloaliphatic, heterocyclic backbones, and a combination thereof.

In another embodiment, the cured epoxy resins are selected from the group consisting of: a cresol-Novolac epoxy resin; a phenol Novolac epoxy resin; a bisphenol F epoxy resin; a polynuclear phenol-glycidyl ether-derived resin; a tetraglycidylmethylenedianiline-derived resin; a triglycidyl-p-aminophenol derived resin; a triazine-derived resins; and a hydantoin epoxy resin.

In another embodiment, the cured epoxy resins are prepared with a curing agent selected from the group consisting of: short chain aliphatic polyamines; oxyalkylated short chain polyamines; long chain polyamine adducts; aromatic polyamines; polyaminoamides; polythiols; and a combination thereof.

In another embodiment, the coating is derived from one or more epoxies that are heat or UV-curable epoxies.

In another embodiment, the coating polymers contain silicone rubber.

In another embodiment, the silicon rubber is a room temperature vulcanizing rubber.

In another embodiment, the coating polymers are comprised of a chemical component of pulp.

In another embodiment, the chemical component of pulp is selected from the group consisting of: starch, lignin, cellulose, hemicellulose, chemically modified starch, lignin, cellulose, hemicellulose, and a combination thereof.

The methodology optionally provides for taking corrective action to change one or more process parameters, or chemistry applied to the process, or a combination thereof, to achieve a desired result in regards to microbiological deposition.

Various apparatuses and algorithms may be used facilitate deposition monitoring.

In one embodiment, the monitoring is realized by using an array/plurality of sensors with one or more coatings to enhance or prevent the deposition of specific contaminants, optionally wherein said monitoring is an on-line monitoring protocol.

In another embodiment, the array of sensors includes a coating containing one for organic monitoring (non-specific to a type of organic species); a coating containing a nutrient for microbiological enhancement; and a coating containing a biocide for suppression of microbiological growth.

By using various types of sensors and applying various types of coatings, one of ordinary skill in the art, can create one or more protocols to differentiate various types of deposits; for example, various types of microbiological deposits can be measured by supplying the sufficient media for suppression or expression of various types of microbiological deposits that are in the papermaking system. In addition, one or more protocols may be created to differentiate non-biological deposits from biological deposits, e.g. inorganic deposits from different types of bacteria.

Using a plurality of sensors, including QCM sensors, one can facilitate the differentiation that one of ordinary skill in the art would like to accomplish.

Additionally, differentiation includes looking at distinction between biological, organic, and inorganic species at various scale levels such as at the micro/macro/nano level, e.g. macrostickies versus microstickies.

In one embodiment, the array of sensors includes a composition containing one for organic monitoring; a composition containing a nutrient for microbiological enhancement; and a composition containing a biocide for suppression of microbiological growth.

In another embodiment, the closed-loop microbiological control is based on information from at least one of the sensors, according to an algorithm developed for microbiological control; optionally wherein said control includes regulating the feeding of chemicals that inhibit microbiological growth. One of ordinary skill in the art would be able to develop an algorithm of interest so that a desired protocol is implemented for the process of interest. A controller may be programmed with said algorithm (e.g. a program logic controller, wherein said controller processes said algorithm to either display via a medium a course of action to be taken/or data for a processor of said process to analyze and respond to, or said controller can signal via a medium that contains the means to alter an action taken on the process, e.g. a feeding strategy.

The following example is a prophetic example.

EXAMPLE

In an example experiment using the novel detection method, flowing slurry containing natural and synthetic organic contaminants such as pitch and stickies, as well as a variety of bacterial strains is passed over an array of QCM sensors. Deposits from pitch, stickies, bulk biofilm, and bacteria are monitored using specific, customized coatings on the surface of the QCM sensors. Using an array of sensors with coatings to enhance or prevent the deposition of specific contaminants, the deposits are differentiated, enabling the real time monitoring of the system.

We claim:

1. A method for monitoring one or more deposits including microbiological deposits on a surface immersed in an aqueous medium of a process comprising:
   a. providing a QCM that is in contact with an aqueous medium, wherein said QCM has a top side surface contacting the aqueous medium, and a second, bottom side surface isolated from the aqueous medium;
   b. providing a composition that is selective for one or more deposit types comprising microbiological deposits, the composition without the use of an antigen or an antibody, wherein the composition comprises one or more nutrients and/or biocides;
   c. applying said composition to the top side of said QCM surface;
   d. measuring the rate of deposition of said deposits from the aqueous medium onto the top side of said QCM surface; and
   e. optionally taking corrective action to change one or more process parameters, or chemistry applied to the process, or a combination thereof, to achieve a desired result in regards to microbiological deposition.

2. The method of claim 1, wherein said process is a papermaking process.

3. The method of claim 1, wherein said aqueous medium is pulp slurry and/or waters from any stage of a papermaking process.

4. The method of claim 1, wherein said nutrients are selected from the group consisting of: biosynthesis metabolites; carbohydrates; polysaccharides; amines; organic acids; alcohols; inorganic nitrogen, sulfur, potassium, sodium, calcium, magnesium, phosphorous, iron, copper, manganese compounds; and a combination thereof.

5. The method of claim 1, wherein said composition contains one or more elements for promoting and/or suppressing microbiological growth of one or more microorganisms that deposit from the aqueous medium onto or grow on the top side of the QCM surface.

6. The method of claim 5, wherein the composition applied to the QCM surface contains at least one of the following compositions: halogen based biocides; hypochlorites; hypobromites; chloroamines; bromoamines; chlorosulfamates; bromosulfmates; aldehydes; parabens; acid-anionic compounds; diamines; metals; quaternary ammonium compounds; chlorohexadine; dyes; alcohols; phenols; cresols; organic acids; and esters.

7. The method of claim 5, wherein the composition applied to the QCM surface contains one or more components that suppresses the growth rate of one or more bacteria, and wherein said components are selected from at least one of following chemistries: biocides, surfactants, polymers, organic acids, and a combination thereof.

8. The method of claim 5, wherein the composition applied to the surface of the QCM promotes the growth of one or more microorganisms, and wherein the composition is selected from the group consisting of: iron salts for filamentous bacteria; lactic acid and/or sulfate for sulfate reducing bacteria; and starch and cellulose for species common to paper machine fouling.

9. The method of claim 8, wherein the filamentous bacteria is selected from the group consisting of: *Sphaerotillus, Crenothrix, Leptothrix*, and *Gallionella*.

10. The method of claim 1, wherein said composition further comprises one or more coating polymers.

11. The method of claim 10, wherein said coating polymers are cured epoxy resins containing one or more epoxy resins and one or more curing agents.

12. The method of claim 11, wherein said epoxy resins are derived from epichlorohydrin and bisphenol A; and resins containing aromatic, aliphatic, cycloaliphatic, heterocyclic backbones, and a combination thereof.

13. The method of claim 11, wherein said cured epoxy resins are selected from the group consisting of: a cresol-Novolac epoxy resin; a phenol Novolac epoxy resin; a bisphenol F epoxy resin; a polynuclear phenol-glycidyl ether-derived resin; a tetraglycidylmethylenedianiline-derived resin; a triglycidyl-p-aminophenol derived resin; a triazine-derived resins; and a hydantoin epoxy resin.

14. The method of claim 11, wherein the cured epoxy resins are prepared with a curing agent selected from the group consisting of: short chain aliphatic polyamines; oxyalkylated short chain polyamines; long chain polyamine adducts; aromatic polyamines; polyaminoamides; polythiols; and a combination thereof.

15. The method of claim 10, wherein said coating polymers contain silicone rubber.

16. The method of claim 15, wherein said silicone rubber is a room temperature vulcanizing rubber.

17. The method of claim 10, wherein said coating polymers are comprised of a chemical component of pulp.

18. The method of claim 17, wherein said chemical component of pulp is selected from the group consisting of: starch; lignin; cellulose; hemicellulose; chemically modified starch; lignin; cellulose; hemicellulose; and a combination thereof.

19. The method of claim 1, wherein the monitoring is realized using an array of sensors with said compositions, wherein the composition applied to the top side of the QCM surface enhances or prevents the deposition of specific contaminants, optionally wherein said monitoring is an on-line monitoring protocol.

20. The method of claim 19, wherein said array of sensors includes a composition containing one for organic monitoring; a composition containing a nutrient for microbiological enhancement; and a composition containing a biocide for suppression of microbiological growth.

21. The method of claim 19, wherein a closed-loop microbiological control is based on information from at least one of the sensors, according to an algorithm developed for microbiological control; optionally wherein said control includes regulating the feeding of chemicals that inhibit microbiological growth.

* * * * *